United States Patent [19]

Eleazar et al.

[11] 4,433,191

[45] Feb. 21, 1984

[54] SKELETAL ISOMERIZATION OF N-ALKENES

[75] Inventors: Antonio E. Eleazar, Freehold; Ronald M. Heck, Frenchtown; Joseph C. Dettling, Howell Township, Monmouth County; Yiu-Kwan Lui, Parlin, all of N.J.

[73] Assignee: Engelhard Corporation, Iselin, N.J.

[21] Appl. No.: 430,297

[22] Filed: Sep. 30, 1982

[51] Int. Cl.³ .............................. C07C 5/28; C07C 5/30
[52] U.S. Cl. .................................... 585/671; 208/139; 585/664; 502/229
[58] Field of Search ..................... 252/442; 208/139; 585/664, 665, 666, 667, 668, 669, 670, 671

[56] References Cited

U.S. PATENT DOCUMENTS

| | | | |
|---|---|---|---|
| 2,397,639 | 4/1946 | Berg et al. | 585/671 |
| 3,511,773 | 5/1970 | Addison et al. | 208/139 |
| 3,717,586 | 2/1973 | Suggitt et al. | 208/139 |
| 4,018,669 | 4/1977 | Hayer et al. | 208/139 |
| 4,061,592 | 12/1977 | Buss | 208/139 |
| 4,213,849 | 7/1980 | Engelhard et al. | 585/671 |
| 4,305,811 | 12/1981 | Johnson | 208/139 |
| 4,306,963 | 12/1981 | Johnson | 208/139 |

FOREIGN PATENT DOCUMENTS

| | | | |
|---|---|---|---|
| 1194833 | 3/1958 | Fed. Rep. of Germany | 208/139 |
| 1420910 | 5/1969 | Fed. Rep. of Germany | 208/139 |
| 2059619 | 12/1970 | Fed. Rep. of Germany | 585/670 |
| 2801841 | 1/1977 | Fed. Rep. of Germany | 208/139 |
| 51-15044 | 5/1976 | Japan | 208/139 |
| 1267719 | 3/1972 | United Kingdom | 585/671 |
| 2032454 | 5/1980 | United Kingdom | 208/139 |
| 722886 | 3/1978 | U.S.S.R. | 585/671 |
| 82/03188 | 9/1982 | PCT Int'l Appl. | 585/671 |

*Primary Examiner*—Delbert E. Gantz
*Assistant Examiner*—A. Pal

[57] ABSTRACT

A novel process for the efficient, selective and steady conversion of n-alkenes, such as n-butylenes, to their skeletal isomers is disclosed. Catalysts and catalytic conditions are also disclosed.

10 Claims, No Drawings

SKELETAL ISOMERIZATION OF N-ALKENES

BACKGROUND OF THE INVENTION

This invention relates to methods for producing skeletal isomers from olefins such as normal or n-alkenes used in the petroleum and fuel industries. More particularly, this invention relates to methods for producing isobutylene from a feedstock comprised of n-butylenes.

As is known, butylene or butene exists in four isomers: butylene-1, cis-butylene-2, its stereo-isomer trans-butylene-2, and isobutylene. Conversions between the butylenes-2 is known as geometric isomerization, whereas that between butylene-1 and the butylenes-2 is known variously as position isomerization, double-bond migration, or hydrogen-shift isomerization. The aforementioned three isomers are not branched and are known collectively as normal or n-butylenes. Conversion of the n-butylenes to isobutylene, which is a branched isomer, is widely known as skeletal isomerization. The same general terminology is used when discussing skeletal isomerization of other n-alkenes and olefins, as well as paraffinic compounds such as n-alkanes.

Isobutylene has become more and more important recently as one of the main raw materials used in the production of methyl tert-butyl ether (MTBE), an environmentally-approved octane booster to which more and more refiners are turning as metallic additives are phased out of gasoline production. However, skeletal isomerization of olefins e.g., to produce isobutene, are relatively non-selective, inefficient, and short-lived because of the unsaturated nature of these compounds. On the other hand, positional and skeletal isomerization of paraffins and alkyl aromatics are fairly well established processes, in general, utilizing catalysts typically comprising metallic components and acidic components, under substantial hydrogen pressure. Since paraffins and aromatics are stable compounds, these processes are quite successful. The heavier the compounds, in fact, the less severe the operating requirements.

Olefins, however, are relatively unstable compounds. Under hydrogen pressure, they are readily saturated to the paraffinic state. Indeed, three processes could be combined for the conversion of n-alkenes to isoalkenes, for example: first, hydrogenation of olefins into paraffins; second, skeletal isomerization of the paraffins; and third and finally, dehydrogenation of the skeletal paraffins in to the desired iso-olefin. In this process combination, the first and third processes are accompanied by large heat effects and therefore may require several stages each; for light hydrocarbons, the conditions for the third process of the combination are usually quite severe.

Furthermore, in the presence of acidity, olefins can polymerize, crack and/or transfer hydrogen. Extensive polymerization would result in poor yields, and short operating cycles. Similarly, cracking would reduce yield. Hydrogen transfer would result in saturated and highly unsaturated compounds the latter being the common precursors for gum and coke. Any theoretical one step process for producing skeletal isomers of, for example, n-butylenes would have to be concerned with the unwanted production of butanes and the reverse problem of production of butadienes. On top of all of these problems, it is well known that skeletal isomerization becomes more difficult as hydrocarbons get lighter.

Representative, for example, of the above prior art isomerization efforts, Myers, U.S. Pat. No. 3,979,333, discloses a catalytic process for the skeletal isomerization of acyclic paraffins and naphthenes. The catalyst contains a Group VIII metal on alumina, which is activated by a gas comprising a mixture of different types of halides.

British Pat. No. 953,187 teaches a catalytic process for the isomerization of $C_4$ and higher paraffins, utilizing a catalyst comprising a hydrogen-containing alumina, a Group VIII metal and halogen compounds, in which process fairly high levels of hydrogen-to-hydrocarbon ratios are employed.

Rausch, U.S. Pat. No. 3,642,925 discloses a method and catalyst for effecting both positional and skeletal isomerization of hydrocarbons including $C_4$–$C_7$ paraffins and olefins. A relatively complex dual-function catalyst is employed, comprising at least five components: a zeolite-type base; a tin component; a Group VIII metal, preferably platinum; a rhenium component; and preferably a halogen component. Skeletal isomerization of butanes is exemplified.

Hayes, U.S. Pat. No. 3,919,340 discloses positional isomerization of olefins and positional and skeletal isomerization of paraffins, cycloparaffins, and alkylaromatics. Once again, a relatively complex dual-function catalyst is utilized comprising five components: a zeolite-type base carrier; a Group VIII metal; an iridium component; a germanium component; and a halogen component. It is important that the Group VIII metal and the iridium be present in elemental metallic states, and that substantially all of the germanium be present in the oxidation state.

Manara et al, U.S. Pat. No. 4,038,337 discloses a method for the skeletal isomerization of alkenes, and specifically discloses the conversion of n-butenes to other n-butenes and iso-butene. The catalyst utilized is obtained by reacting an active alumina with an ester of silicic acid, preferably the lower alkyl esters of orthosilicic acid. It has been found that the latter process generally has a short-cycle length between regenerations, sometimes as little as one day. Additionally, high temperatures are generally required, usually exceeding 450° C.

Because of the increasing importance to the fuel and petroleum industries of the availability of a process which efficiently and readily produces isoalkenes from feedstocks containing n-alkenes, it is a principal object of this invention to design such a process which does not require frequent regeneration and high temperature. It is a further object of this invention to design such a process which strikes a desirable balance between the production of isoalkenes on the one hand, and the repression of the production of their corresponding carbon-number alkanes on the other hand.

SUMMARY OF THE INVENTION

The method of this invention achieves these and other purposes, and comprises, feeding an n-alkene by itself or in admixture with other hydrocarbons into a reactor vessel containing an isomerization catalyst, wherein the catalyst consists essentially of a Group VIII metal-on-alumina base, optionally preferably pretreated with a halide or halide mixture. Preferably, n-alkane having the same carbon number as the n-alkene is included, in the feedstock. Relatively low pressures of hydrogen are maintained in order to suppress production of coke-forming hydrocarbons, e.g., butadiene.

N-alkene conversions of 30–50%, or higher, iso-alkene selectivities of 50–85%, or higher, and iso-alkene yields of 15–35%, or higher are possible with the method of this invention.

DESCRIPTION OF THE INVENTION

The method of this invention makes use of catalysts which are comprised of two key components treated with a third, the general combination of which is known to the hydrocarbon isomerization or separation arts. Catalysts preferred for use comprise a mixture or coating of a Group VIII metal on an activated alumina oxide, in a range of about 0.1 to 10%, preferably 0.5 to 2% of the metal per weight of the oxide. By activated aluminum oxide is meant one having a surface area of at least about 100, preferably at least about 250, and most preferably at least 300 square meters per gram. The preferred Group VIII metal is palladium or platinum. Most preferred is palladium.

In the method of this invention, the metal-on-alumina base is preferably heat treated with a halide-containing vapor in order to deposit halide on the catalyst alumina base, at a level of about 4 to 20%, preferably 5 to 10% halide per weight of alumina. A preferred method of depositing the halide layer comprises bubbling air through a liquid halide and then directing the air-halide mixture through the reactor vessel. It is not critical to this invention how the halide is deposited on the catalyst base. Other variations known to the art will suffice. Where the air treatment is used, the catalyst is preferably heated to a temperature of from about 250° to 300° C. during halide deposition.

Organic halides are preferred for treating the catalyst, such as carbon tetrachloride, trichloroethylene, etc. As before stated, any method of, and any halide suitable for, depositing the halide on the base is embraced within the practice of this invention.

Catalysts thus constituted are then basically prepared for skeletal isomerization as below described. While the thrust of the invention is to branch-isomerize n-butenes, any isomerizable n-alkenes may be successfully converted by this invention. The olefin feedstock may be pure n-alkene, or, in the preferred aspect, additionally contains n-alkanes of about the same carbon number as the n-alkene to be treated. In addition the feed preferably contains a halogenated compound in small amounts, i.e. 50 to 5000 ppm. Suitable such compounds include the same as used to treat the catalyst. As indicated, the primary motivation is to skeletally isomerize n-butenes, and the examples will illustrate the invention with reference to feedstocks containing this type of olefin.

EXAMPLE I

The preparation of a catalyst for use in the method of this invention is illustrated as follows:

A catalyst comprising 1% palladium on eta-alumina is charged into a reactor. Air is passed through a moisture trap and then through the reactor, while the catalyst is heated to about 260° C. This step is intended to dry out the catalyst in order to insure that the halide subsequently introduced will be adsorbed onto the alumina. This air-drying procedure lasts about one hour at a space velocity of about 800 per hour at atmospheric pressure.

The dry air is then mixed with dry carbon tetrachloride vapor before entering the reactor. Fumes are observed in the reactor effluent, which are allowed to subside. The air/chloride mixture is passed through the reactor for about one hour, with the reactor inlet temperature maintained at about 260° C., at a space velocity of 800 per hour. This results in a deposition of about 6.5% chloride per weight of the catalyst.

After this treatment, the chloride is by-passed and the air treatment is repeated this time to purge unreacted chloride and any impurities introduced therewith.

EXAMPLE II

Halide-treated catalysts are then subjected to an isomerization start-up procedure as follows.

Again, the temperature of the catalyst is adjusted to about 260° C. The reactor is purged with nitrogen to remove oxygen from the system. Then the reactor is pressurized with dry n-butane to about 50 psig, a step which will help control the temperature of the catalyst and keep it from going too high when the olefin feed commences. It is desirable to keep the temperature below the level where coke buildup becomes too rapid. Dry olefin feed is then started at about 2 per hour weight velocity. Exotherms are then allowed to subside and the hydrogen feed begins. Preferred hydrogen partial pressures range from about 1–100 psia.

After any exotherm from the hydrogen feed has subsided, the temperature of the catalyst is adjusted to about 300° C. The catalyst is then ready for steady-state isomerization.

EXAMPLE III

Using a catalyst prepared as in Examples I and II, technical-grade butene-2 was fed into the reactor with 2000 ppm carbon tetrachloride. The temperature of the vessel was adjusted to about 350° C. at about 250 psig total pressure. Hydrogen was fed into the reactor at a pressure of 60 psia. It will be noted that this level of hydrogen is relatively much lower than previous levels used in the prior art. Two runs were made in this manner at a butene feed space velocity of about 0.5 per hour. The results are as tabulated below:

|  | Run #1 | Run #2 |
|---|---|---|
| Conversion (%) | 31 | 30 |
| Selectivity (%) |  |  |
| $C_3-$ | 2 | 2 |
| n-butane | 16 | 14 |
| isobutane | 3 | 3 |
| isobutene | 64 | 55 |
| $C_5$ | 3 | 2 |
| $C_6$ (wt. %) | 6 | 24 |

Thus, using a pure feed of butene-2, yields of the branched isomer were 19.8% and 16.5% respectively.

EXAMPLE IV

The types of feedstocks to be expected in commercial-scale skeletal isomerization processes will contain significant portions of paraffinic analogues to the olefinic material to be isomerized. Thus several runs were made using catalysts prepared as in Examples I and II with the butene-2 feed mixed with n-butane in percentages as indicated in the tables below. The temperatures were again adjusted to about 350° C., feed was 0.5 per hour, pressures were as indicated. The results were:

| $H_2$/pressure, psia | 60 | 16 |
|---|---|---|
| n-butane feed (%) | 0.7 | 42.8 |
| pressure (psig total) | 156 | 180 |

| -continued | | |
|---|---|---|
| Conversion (%) | 30.5 | 34.1 |
| Selectivity (%) | | |
| C$_3$− | 1 | 1 |
| n-butane | 16 | 4 |
| isobutane | 2 | 2 |
| isobutene | 78 | 85 |
| amylenes | 1 | 2 |
| C$_6$+ (wt %) | 2 | 6 |

As clearly represented, increasing the amount of n-butane in the feed from 0.7 to 42.8% of the butene-2 resulted in an increase in the yield from butene-2 to the skeletal isomer of 23.8 to 29%. This indicates that the efficiency of the inventive process increases as the feedstock more closely resembles that which will be encountered in industrial applications.

EXAMPLE V

Several runs were made with different pressures, utilizing a feed of 47%/53% n-butane/butene-2. Temperatures were adjusted to, and maintained at, between 350° and 375° C. H$_2$ feeds were as indicated as are the pressures. Feed velocity was 0.5 per hour. The results:

| Time in cycle hr. | 502 | 651 | 682 |
|---|---|---|---|
| H$_2$/pressure, psia | 16 | 5 | 22 |
| Pressure (psig total) | 180 | 360 | 360 |
| Conversion (%) | 34 | 44 | 51 |
| Selectivity (%) | | | |
| C$_3$− | 1 | 2 | 3 |
| n-butane | 4 | 2 | 3 |
| isobutane | 4 | 2 | 3 |
| isobutene | 85 | 78 | 74 |
| amylenes | 2 | 2 | 3 |
| C$_6$+ | 6 | 13 | 13 |

Clearly, using feedstocks of commercial composition, even greater skeletal isomerization values are obtained when the total pressure was increased by a factor of 2, as in Runs 2 and 3, specifically from 29% to 34 and 38% respectively. Generally lower amounts of hydrogen were needed when the total pressure was doubled.

What is claimed is:

1. A method for converting a linear isomerizable olefin to its branched isomers, comprising, passing the linear olefin in admixture with its paraffinic analogue throught a vessel containing an isomerization catalyst consisting essentially of a Group VIII metal on an activated alumina base, and a halide absorbed thereon at a pressure and at a temperature sufficient to convert at least 15% of the linear olefin to its skeletal isomer.

2. The method of claim 1 wherein the vessel is held at a pressure of from 1 to 40 atmospheres at a temperature of from 250°–400° C.

3. The method of claim 1 wherein the admixture further contains about 50 to 5000 ppm of a halogenated compound.

4. The method of claim 3 wherein the vessel additionally contains from 1 to 100 psia hydrogen during isomerization, and wherein at least 20% of the linear olefin is converted to its skeletal isomer.

5. The method of claim 4 in which the olefin is n-butene or a mixture of same.

6. The method of claim 5 in which the paraffin is n-butane or a mixture of butanes.

7. The method of claim 6 in which the amount of n-butane fed into the vessel is up to about 60% of the total of n-butane and n-butene.

8. A method for converting a linear isomerizable olefin to its branched isomers, comprising, passing the linear olefin through a vessel containing an isomerization catalyst consisting essentially of a Group VIII metal and a halide adsorbed onto an activated alumina base, at a pressure and at a temperature sufficient to convert at least 15% of the linear olefin to its skeletal isomer.

9. The method of claim 8 wherein the vessel is held at a pressure of from 1 to 40 atmospheres at a temperature of from 250°–400° C.

10. The method of claim 8 wherein the vessel additionally contains from 1–100 psia hydrogen during isomerization, and wherein at least 20% of the linear olefin is converted to its skeletal isomer.

* * * * *